(12) United States Patent
Fenton, Jr.

(10) Patent No.: US 6,423,088 B1
(45) Date of Patent: Jul. 23, 2002

(54) SHARP EDGED DEVICE FOR CLOSING WOUNDS WITHOUT KNOTS

(75) Inventor: Paul V. Fenton, Jr., Marblehead, MA (US)

(73) Assignee: Axya Medical, Inc., Beverly, MA (US)

( * ) Notice: Subject to any disclaimer, the term of this patent is extended or adjusted under 35 U.S.C. 154(b) by 0 days.

(21) Appl. No.: 09/607,880

(22) Filed: Jun. 30, 2000

Related U.S. Application Data (63) Continuation-in-part of application No. 09/349,663, filed on Jul. 8, 1999
(60) Provisional application No. 60/141,741, filed on Jun. 30, 1999, provisional application No. 60/092,072, filed on Jul. 8, 1998, and provisional application No. 60/092,074, filed on Jul. 8, 1998.

(51) Int. Cl.[7] ............................................. A61B 17/04
(52) U.S. Cl. ........................................................ 606/232
(58) Field of Search .............................. 606/213, 214, 606/215, 216, 217, 219, 220, 232, 151, 152, 153, 155, 157; 24/114.6, 304

(56) References Cited

U.S. PATENT DOCUMENTS

| | | |
|---|---|---|
| 3,113,408 A | 12/1963 | Kirkpatrick et al. |
| 3,407,777 A | 10/1968 | Anastasio et al. |
| 3,462,803 A | 8/1969 | Horton |
| 3,503,119 A | 3/1970 | Seitz, Jr. et al. |
| 3,513,848 A | 5/1970 | Winston et al. |
| 3,516,631 A | 6/1970 | Santucci |
| 3,664,345 A | 5/1972 | Dabbs et al. |
| 3,802,438 A | 4/1974 | Wolvek |
| 3,857,396 A | 12/1974 | Hardwick |
| 3,879,981 A | 4/1975 | Richards |
| 3,995,870 A | 12/1976 | Hulek |
| 4,050,100 A | 9/1977 | Barry |
| 4,291,698 A | 9/1981 | Fuchs et al. |
| 4,561,153 A | 12/1985 | Matsui |
| 4,588,408 A | 5/1986 | Yamada |
| 4,693,249 A * | 9/1987 | Schenck et al. ............ 128/334 |
| 5,078,731 A | 1/1992 | Hayhurst |
| 5,356,417 A | 10/1994 | Golds |
| 5,376,101 A | 12/1994 | Green et al. |
| 5,383,883 A | 1/1995 | Wilk et al. |
| 5,383,905 A | 1/1995 | Golds et al. |
| 5,391,173 A | 2/1995 | Wilk |
| 5,413,585 A | 5/1995 | Pagedas |
| 5,417,700 A | 5/1995 | Egan |
| 5,425,489 A | 6/1995 | Shichman et al. |
| 5,437,685 A | 8/1995 | Blasnik |
| 5,500,018 A | 3/1996 | Spotorno et al. |
| 5,527,341 A | 6/1996 | Gogolewski et al. |
| 5,586,983 A | 12/1996 | Sanders et al. |
| 5,593,425 A | 1/1997 | Bonutti et al. |
| 5,611,801 A | 3/1997 | Songer |
| 5,618,311 A | 4/1997 | Gryskiewicz |
| 5,643,289 A | 7/1997 | Sauer et al. |

(List continued on next page.)

Primary Examiner—Eduardo C. Robert
(74) Attorney, Agent, or Firm—McDermott, Will & Emery (57) ABSTRACT

A device for closure of a living tissue wound without requiring knots. The device is a resiliently flexible and fusible collar having a C-shaped side profile disposed about a central region extending along a central axis. The collar extends circumferentially between two end portions for containing at least a portion of two tissue edges forming a tissue wound. The collar is biasable into a nominally closed O-shape so that the end portions overlap and tissue edges therein are joined together to close the tissue wound. The overlapping end portions are adapted to be fused together upon application of sufficient energy to the overlapping end portions to maintain the tissue edges in a joined position. The collar has a width greater than a thickness of the collar to increase the area of fusion between the overlapping end portions. In addition, at least one of the end portions of the collar has a sharp edge for tissue penetration so that the collar can be used to close open tissue wounds.

19 Claims, 9 Drawing Sheets

U.S. PATENT DOCUMENTS

| | | |
|---|---|---|
| 5,732,530 A | 3/1998 | Pfaff |
| 5,735,877 A | 4/1998 | Pagedas |
| 5,749,895 A * | 5/1998 | Sawyer et al. ............... 606/214 |
| 5,766,218 A | 6/1998 | Arnott |
| 5,769,894 A | 6/1998 | Ferragamo |
| 5,779,720 A * | 7/1998 | Walder-Utz et al. ........ 606/151 |
| 5,881,452 A | 3/1999 | Nowell, III et al. |
| 5,893,880 A | 4/1999 | Egan et al. |
| 5,922,026 A * | 7/1999 | Chin ........................... 623/11 |
| 5,941,901 A | 8/1999 | Egan |

* cited by examiner

SHARP EDGED DEVICE FOR CLOSING WOUNDS WITHOUT KNOTS

CROSS REFERENCE TO RELATED APPLICATIONS

This application is a continuation of provisional U.S. application Ser. No. 60/141,741, filed Jun. 30, 1999, the disclosure of which is hereby incorporated by reference into this application. This application is also a continuation in part of U.S. application Ser. No. 09/349,663, filed Jul. 8, 1999, which is a continuation in part of provisional U.S. applications Ser. Nos. 60/092,072, and 60/092,074, both filed Jul. 8, 1998. The disclosure of U.S. application Ser. No. 09/349,663 is hereby incorporated by reference into this application.

FIELD OF THE INVENTION

The present invention relates generally to devices and methods for joining sutures without knots, and for securing living tissue structures together without sutures. The present invention also relates to devices and methods for closing wounds without knots.

BACKGROUND OF THE INVENTION

In minimally invasive surgical procedures that use elongated instruments and videoscopic viewing of the surgery site, there is a significant elevation in the difficulty of knot tying and wound approximating. Traditional methods of wound closure routinely involve the use of individual hand-knotted sutures. The suture strands are directed through portions of tissue to be joined and formed into a single stitch, which is then knotted. However, due to the location of the area being sutured, the delicate nature of anatomical features, and the stiffness of the suture used, it can be difficult to tie uniform stitches to close the wound that do not unravel or tie off (or ligate) a vessel. Non-uniform stitches (i.e., stitches of varying tension) or varied bite size (depth into the tissue) can cause uneven healing, localized trauma, infection, and patient discomfort.

To reduce the discomfort and aid healing, it is desirable to secure sutures uniformly and close to a wound. Due to the stiffness of some sutures, knotting the sutures can be difficult, particularly when the tissue to be sutured is deep within the body. Typical knots may be relatively large and elevated above the tissue being sutured, which can increase patient discomfort.

It is also desirable in many surgical procedures where sutures are used to reduce the size of the knot bundle and the amount of foreign material in the body. The knot bundle can become an irritant and retard the healing process and cause discomfort or pain for the patient. The knot bundle can also be a source of infection.

Methods known in the art to overcome these problems include various suture securing devices such as buttons, and methods of fusing synthetic sutures. Although buttons can produce sutures with even tension and without the concomitant dexterity of knot tying, their elevated location above the wound or within the body cavity can cause irritation and discomfort. Furthermore, there is a risk of button migration, since they are discrete objects in the body.

Suture fusion techniques, whereby synthetic polymer suture strands are melted together by the application of heat or other energy to the sutures, are known in the art. Examples of devices to perform such suture fusion are disclosed in U.S. Pat. No. 5,417,700, assigned to the assignee of this application and incorporated herein by reference. However, some polymeric sutures are not amenable to this process. For example, braided or multi-filament sutures may not completely fuse since spaces between the individual strands may interfere with the heat or energy transfer needed for fusion to occur. As a result, the sutures may be incompletely fused, and the resulting joint may fail.

It would be advantageous to provide suture and tissue joining devices which are fusible to and/or around sutures and other structures, including living tissue, so as to avoid the need for suture knots.

SUMMARY OF THE INVENTION

The present disclosure accordingly provides a device for closure of a living tissue wound without requiring suture knots. The device is a resiliently flexible and fusible collar having a C-shaped side profile disposed about a central region extending along a central axis. The collar extends circumferentially between two end portions for containing at least a portion of two tissue edges forming a tissue wound. The collar is biasable into a nominally closed O-shape so that the end portions overlap and tissue edges therein are joined together to close the tissue wound. The overlapping end portions are adapted to be fused together upon application of sufficient energy to the overlapping end portions to maintain the tissue edges in a joined position. The collar has a width greater than a thickness of the collar to increase the area of fusion between the overlapping end portions. In addition, at least one of the end portions of the collar has a sharp edge for tissue penetration so that the collar can be used to close open tissue wounds.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

Like features in the figures are labeled with like numerals.

DESCRIPTION OF THE PREFERRED EMBODIMENTS

The present invention provides, in one aspect, a device, kit, and method for securing sutures or anatomical features in human or animal tissue that eliminates the need for tying knots in sutures. The invention is practiced with the aid of a tool that joins a fusible banding device or collar to itself around the sutures or around living tissue structures, such as ligaments, vessels and ducts. Alternatively, the collar can be fused to itself around a number of sutures, which can also be fused to one another. The devices and methods of the invention secure a fusible collar to sutures or living tissue structures close to a wound site so that the sutures can be made taut and secured without coming undone and without the bulk and inconvenience associated with knots and knotting processes, which are difficult, time-consuming and cumbersome in confined spaces. Furthermore, the joining process insures that braided and multi-filament sutures will fuse adequately and remain secure. Various methods of fusing or joining sutures or other elongated structures together joining by the application of energy to the fusible collar are well known in the art and can be employed to secure the band and sutures. Examples of such techniques include, but are not limited to, thermal energy (e.g., heat), optical energy (e.g. laser), electrical (e.g., radiofrequency RF), current sources (e.g., resistive heating), and preferably, ultrasonic energy.

Application of energy to the fusible collar may be carefully controlled, as detailed more fully below, to ensure localized melting and joining of the collar without causing trauma to underlying and nearby tissue structures.

In a preferred form of the invention, the collar is formed as a split, or open, ring-like structure which is made of a biocompatible, flexible material that is adapted to pierce and encircled living tissue. The collar may be resilient or substantially resilient so that after cessation of a deforming force, it returns to substantially its original shape. The collar may have one or more energy directors extending from a surface of the collar to focus energy propagating through the collar at particular areas, or fusion regions, on the collar. The collar may be made in various geometries, but preferably has a rectangular cross-section to provide large regions of contact for fusion during compression of the collar and application of energy thereto.

Throughout the specification, it will be understood that the collar can be used to encircle living tissue structures and cinch or bundle them together, wherein the collar is then fused to itself at an overlap region to secure the bundled structures together. Similarly, the collar can encircle one living tissue structure, such as a blood vessel or duct, then fuse to itself in a manner that restricts the flow of fluid through the structure (ligate). Alternatively, the collar can be used to encircle and secure a plurality of fusible surgical sutures, which can themselves be melted and fused together, and optionally to the collar, upon application of energy to the collar. The collar can also be used to close wounds in living tissue.

Figure 1:
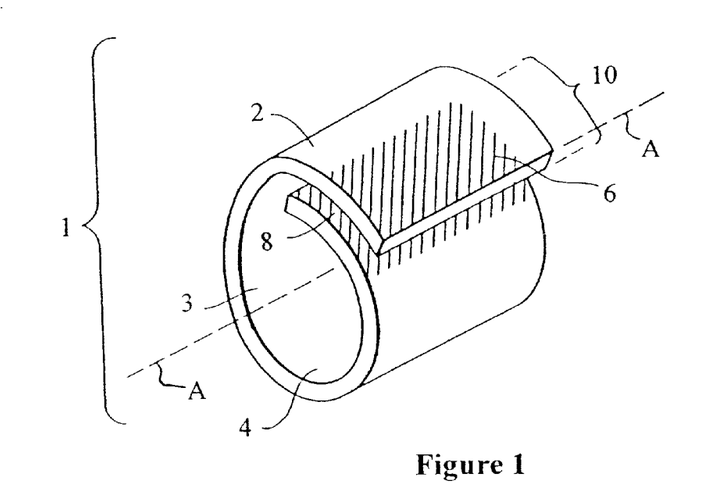
FIG. 1 is an oblique view of a preferred embodiment of a collar according to the present disclosure.

FIG. 1 shows one embodiment of the collar 1 which is formed substantially as a C-shape and which is resiliently biased into a nominally closed O-shape position so as to encircle a generally cylindrical central region 3 extending along central axis A for retaining sutures or living tissue structures. End portion 6 extends circumferentially and overlaps end portion 8 at overlap area 10 to form a tubular structure.

Central region 3 of the tubular structure should be large enough to permit the sutures or tissue structures to be secured therein by the collar so that the end portions 6, 8 overlap. The inner surface 4 of the collar can be smooth, or it can be grooved, have protrusions, or be otherwise textured in some way, to create a roughened surface area to enhance contact between the collar and the structure(s) therein. This latter form is particularly useful when securing a collar to a tissue such as a ligament.

Figure 2A:
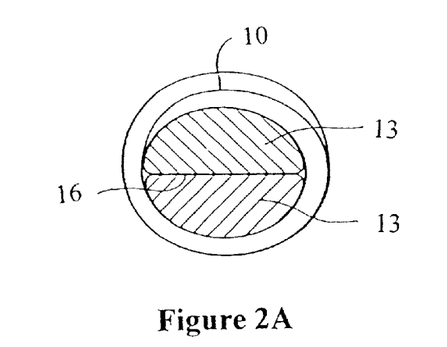
FIG. 2A is a cross-sectional view of the collar of FIG. 1 shown fused around a pair of suture strands.
Figure 2B:
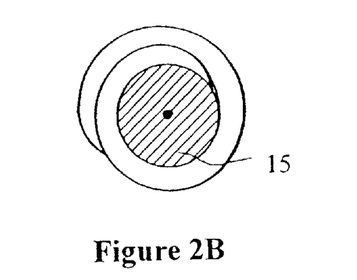
FIG. 2B is a cross-sectional view of the collar of FIG. 1 shown fused around a tubular structure, such as a vessel.

FIG. 2A shows the collar after it has been compressed so that end portions 6, 8 overlap. Following the compression, collar 1 is fused around a pair of sutures 13. Preferably, collar 1 is compressed around the sutures 13, so that the sutures are pressed against each other to the point of deformation, thereby increasing their mutual contact surface areas. FIG. 2B shows the collar compressed around and ligating an anatomical structure, such as a blood vessel 15.

Depending on the selection of materials for the collar and the sutures, fusion can occur in selected regions, i.e., in the overlap region 10 of the collar, between the collar and the sutures at energy directors, discussed more fully below, and at interface regions 16 between the sutures themselves.

The collar is preferably made of a biocompatible material which is sufficiently flexible to allow for moderate deformation of the collar to allow sutures or other anatomical structures to be placed within the collar. The collar may be substantially resilient so that after cessation of a deforming force, it returns substantially to its original shape around the sutures or structures therein. In one form, the material is resilient so as to retain the structures within the collar and create contact surfaces or fusion regions for the welds. Any type of material that meets these requirements can be used.

The collar material is preferably also capable of being fused or joined together upon the application of energy, such as thermal energy (heat), optical energy (laser generated), electrical energy (radio frequency, RF), current sources (resistive heating) or, preferably, ultrasonic energy, to the collar. Preferred materials are synthetic polymers capable of being repeatedly softened or melted with the application of heat or pressure (commonly known as thermoplastics). Thermosetting plastics and other heat-fusible materials may also be suitable for use as a collar under certain conditions. The collar can be made by methods known in the art, such as, but not limited to, machining, injection molding, extrusion, thermoforming and the like.

If desired, a collar made of one material, and sutures made of a different material having a different melting temperature, can be employed together so as to further direct the melting and fusing upon application of energy to the collar. Higher melting point materials may be preferred for the collar, particularly if braided or multi-filament sutures are used, as the bonding energy can fuse underlying fibers as well as the sutures themselves. The energy required to melt the material using the various processes and the time required for the molten material to resolidify are well known in the art.

The suture material can be of any type customarily used for sutures such as silk, but preferred materials are polymers such as PTFE, and especially preferred are thermoplastic materials, such as polyamide (nylon), polypropylene, polyester, polyglycolic acid (PGA), polyglyconate, and polydioxanone. The sutures can be either substantially monofilamentous, multiple stranded, twisted, braided, or otherwise interlinked material. The suture filament can have any cross-sectional shape, for example, substantially circular, elliptical or rectangular.

The choice of materials for the sutures and the collar and the geometry of the collar determines which materials fuse, and where fusing occurs. For example, if a collar and sutures are made from materials with largely differing melting temperatures (for example, collars are thermoset polymers or non polymer material, and the suture strands are thermoplastic polymers), the bonds can occur at the suture to suture interface, and within the individual fibers that make up the suture strand (in the case of a multi filament or braided material), but little or no fusing of sutures to the collar occurs. Conversely, when the collar is made of a thermoplastic material, and the suture is a thermoset polymer, non polymer or when an anatomical feature is within the collar, fusing of the collar to itself at the overlap areas occurs. This could be beneficial for retaining ligaments, vessels or ducts, while allowing the collar to move relative to the ligaments, vessels or ducts retained therein, or for ligating a vessel or duct. In a most preferred embodiment, the collar material and the sutures are both made of a material that melts at similar temperatures (e.g. both are thermoplastic polymers). This allow for bonds to occur at all or any of the contact interfaces described.

Figure 3:
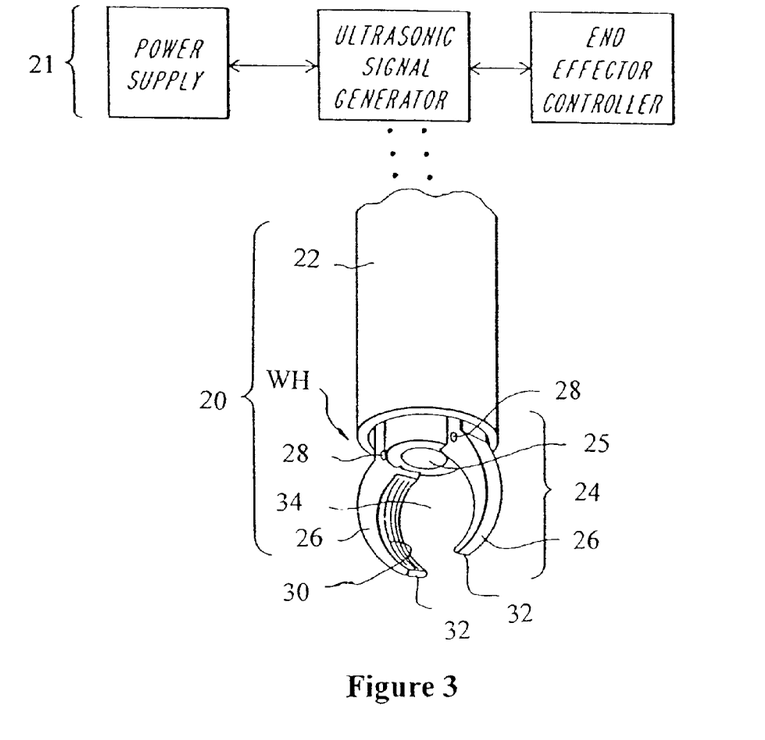
FIG. 3 is an oblique view of a fusing tool for fusing the collar of FIG. 1.
Figure 4:
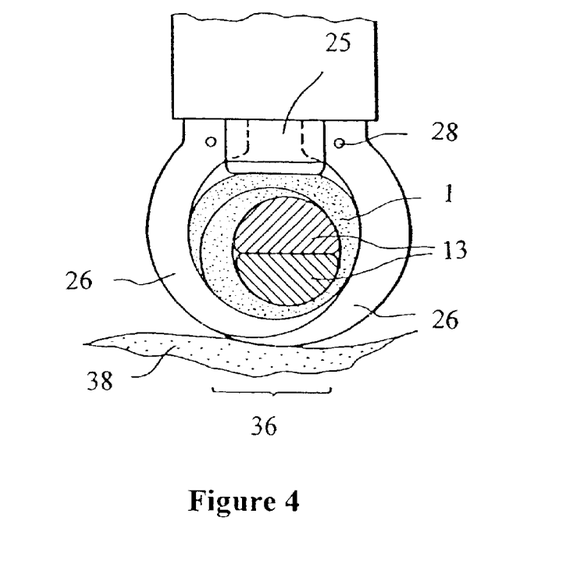
FIG. 4 is an oblique view of an end effector of the fusing tool of FIG. 3 shown positioned around the collar of FIG. 1, which is shown encircling sutures to be fused together with the collar.

The fusing tool used to compress and fuse the collar generally is shown in FIGS. 3 and 4. The fusing tool 20 includes a shaft 22, welding head WH, and end effector 24 adapted to cradle and compress the collar around sutures or structures to be joined. The shaft also connects the welding head and end effector to various control devices 21 and electronics for receiving electrical power and converting it to weld energy, and for moving the end effector. Welding head WH transmits the weld energy to the collar.

In the ultrasonic embodiment, the welding head WH is adapted to intimately contact the surface of the collar when the collar is positioned within the end effector. End effector 24 is mounted to the shaft and surrounds the welding horn.

FIG. 3 shows the fusing tool 20 as it appears in preparation to receive a collar. The fusing tool 20 includes a delivery shaft 22 with end effector 24 attached to the distal end of the delivery shaft at joints 28, which can be pins, hinges or the like. End effector 24 is formed by a pair of curved jaws 26 which move on joints 28 relative to each other to open and close to receive, hold and release the collar 1. Inner surfaces 30 of jaws 26 can be smooth, grooved or otherwise textured to enhance engagement between the jaws and the collar. Welding horn 25 is situated between the joints on delivery shaft 22.

FIG. 4 shows a fusing tool 20 with a collar 1 positioned near tissue 38 for fusing the collar around and to a pair of sutures 13. Jaw ends 32 abut or overlap to form welding anvil 36. Deployment of the jaws around the collar compresses the collar 1 around sutures 13 to maintain tension on the sutures and increase the contact surface area of the suture and collar, allowing for a larger total fused area. To fuse the collar to itself and to the sutures, bonding energy is transmitted from the welding horn 25 to anvil 36, through the collar and the sutures within the collar. The fused collar and encased sutures are released from the jaws when jaws 26 are retracted.

Flattened or rounded ends on the prongs 32 allow for the prongs to abut tissue 38 when the sutures are pulled tight through the collar, such as at a wound site, thereby minimizing any gaps in the tissue to be joined and maintaining a desired tension on the sutures. In one embodiment, the prongs can also function as an anvil. In other embodiments, underlying bone, tissue, anatomical features, or other materials temporarily or permanently placed under the end effector may also act as an anvil. The latter design may be preferable if it is necessary or otherwise advantageous to secure the collar as closely as possible to tissue so as to permit minimal gapping between the joined sutures and the collar.

In another embodiment of the invention, the fusing tool end effector 20 and the collar 1 comprise a kit 200, as shown in FIG. 4. The kit 200 may include various end effectors that are interchangeable on the tool shaft for accommodating different collar shapes and sizes.

Figure 5A:
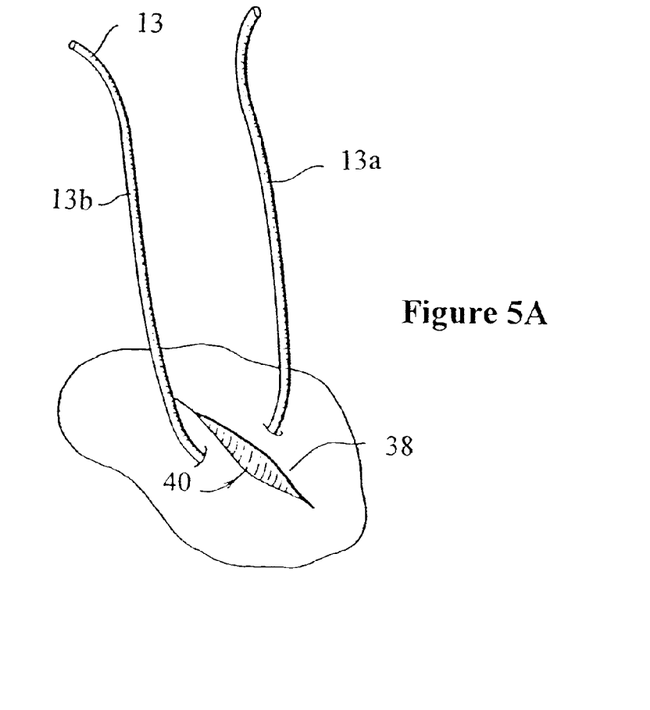
FIGS. 5A–5F are simplified diagrams of a method of securing sutures according to the present disclosure using the collar of FIG. 1 and the fusing tool of FIG. 3.
Figure 5B:
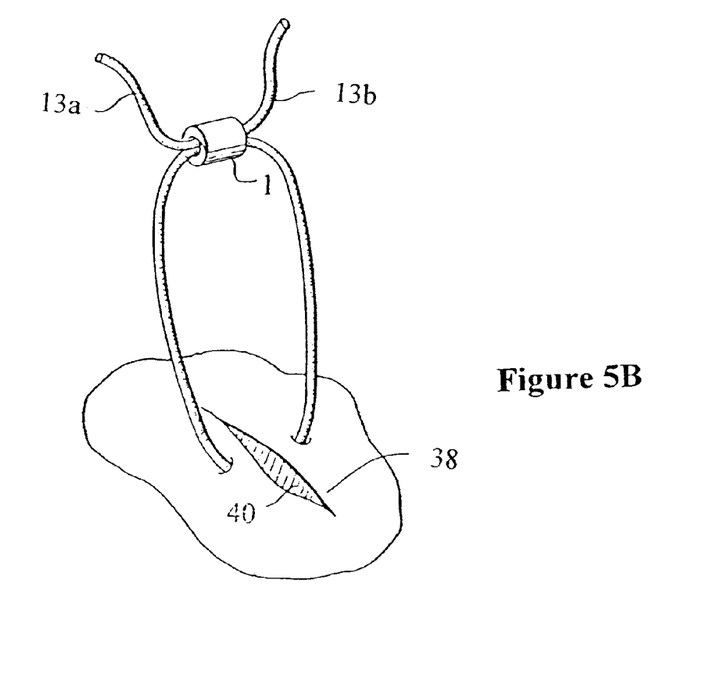
Figure 5C:
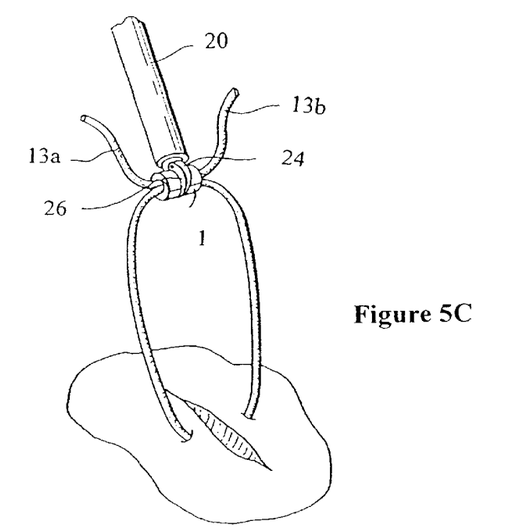
Figure 5D:
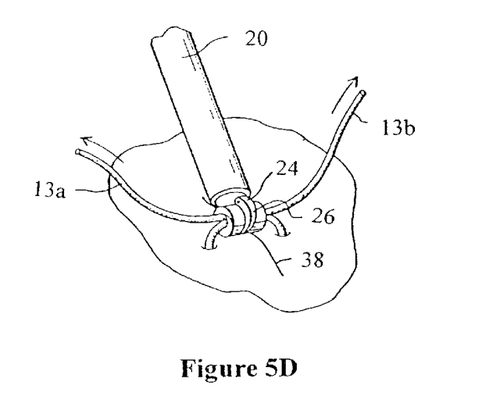
Figure 5E:
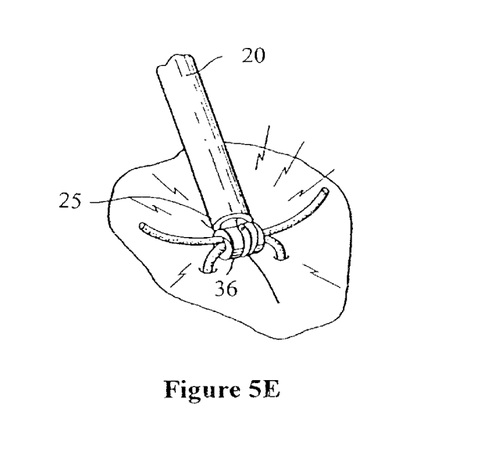
Figure 5F:
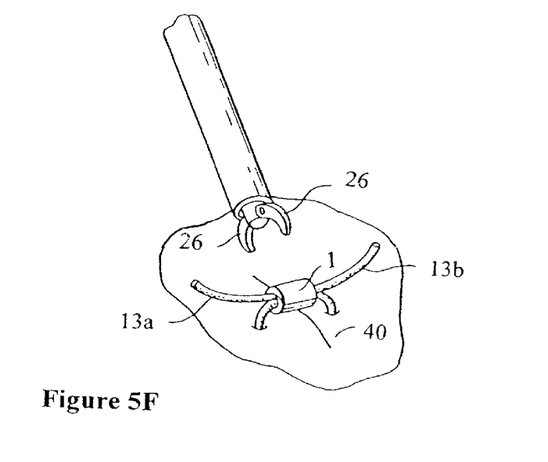

A process for securing suture strands within a fusible collar is demonstrated in FIGS. 5A through 5F using the collar 1 shown in FIG. 1 and the fusing tool 20 of FIG. 3. In FIG. 5A, a suture 13 has been passed through opening or fissure 40 in tissue 38. In FIG. 5B the suture strands 13a,b are threaded in opposite directions through collar 1 prior to fusing. In FIG. 5C, collar 1 is engaged by the jaws 26 of the fusing tool 20. In FIG. 5D, the strands 13a,b are pulled taut in opposite directions as indicated by the arrows, thereby applying tension on opposite edges of the wound fissure 40 to close it. As shown in FIG. 5E, to secure the collar in place for welding and maintain the tension on the suture, the jaws 26 compress the collar 1 around the suture strands. Ultrasonic or thermal energy is transferred from the welding horn 25 to anvil 36 and collar 1, creating localized heat, which melts the collar 1 sufficiently to cause plastic flow and fusing of the collar to itself and to the sutures 13 encased therein. The fused collar remains within the jaws for a short period of time to allow the fused material to re-solidify. FIG. 5F shows jaws 26 retracted from the collar 1 and the fused collar-suture structure in place securing wound 40. Suture strands 13a,b can be trimmed close to the collar without loosening the fused structure.

Figure 6:
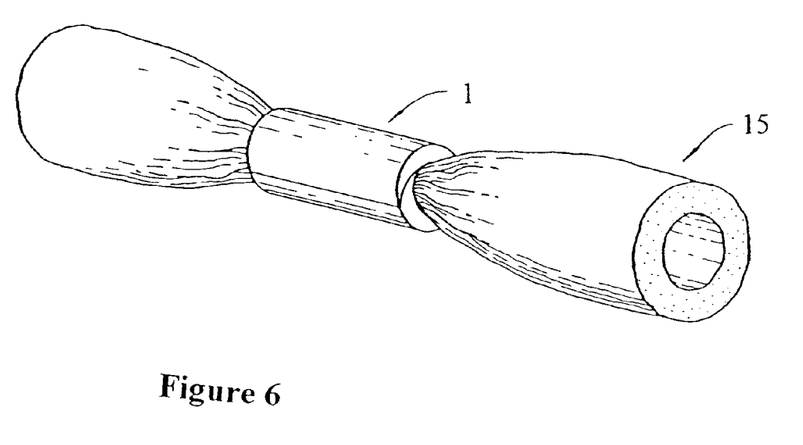
FIG. 6 is an oblique view of the collar of FIG. 1 ligating a vessel.

This method for closing a wound can be employed for other surgical procedures and anatomical structures. For example, the process for ligating a vessel or duct is similar to the one described except that the suture is threaded under or around the vessel or duct rather than through tissue, and the suture is secured with an appropriate collar. Alternatively, a collar can be placed around the vessel or duct, compressed, and fused to itself FIG. 6 shows collar 1 fused to itself around a crimped vessel 15, completing the ligation.

Figure 7:
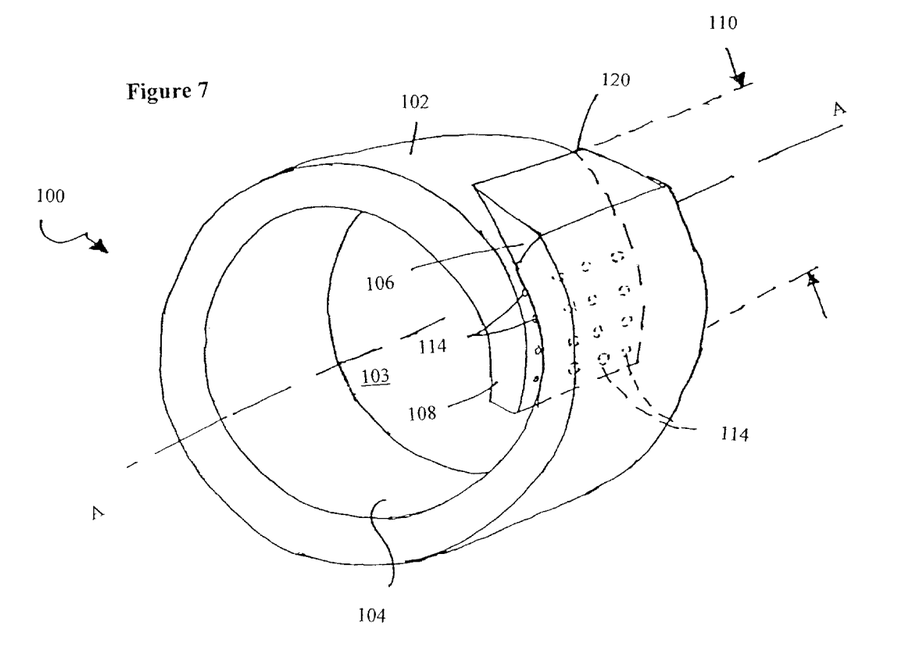
FIG. 7 is an oblique view of another preferred embodiment of the collar.
Figure 8:
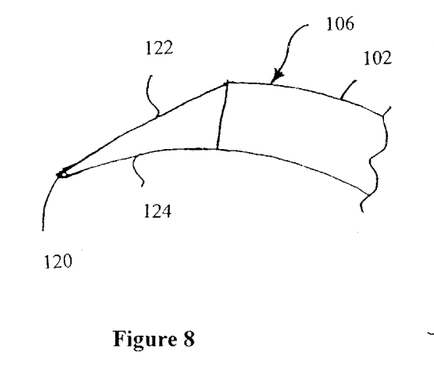
FIG. 8 is a side elevation view of an end portion of the collar of FIG. 7.
Figure 9:
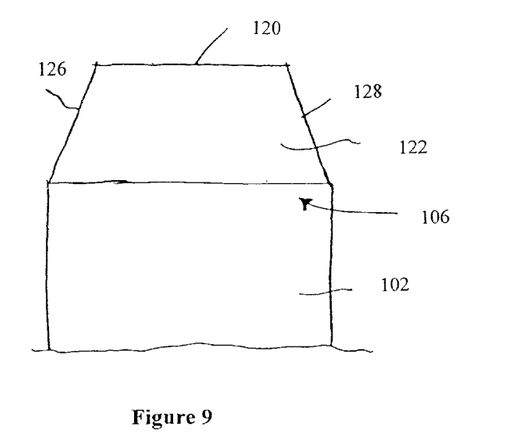
FIG. 9 is a top plan view of the end portion of the collar of FIG. 7.

Referring now to FIGS. 7 through 9, another collar 100 according to the present disclosure is shown. This embodiment 100 contains all the details found in the embodiment 1 of FIG. 1. In addition, at least one of the end portions 106 of the collar 100 is provided with a sharp edge 120 for tissue penetration prior to end portions 108, 106 being fused together. The collar 100 of FIGS. 7 through 9, accordingly, is especially useful in closing unwanted openings, i.e., wounds, in living tissue, and the collar 100 is for use in place of normal sutures such that knots are not required to close tissue wounds.

As shown in FIG. 7, the collar 100 is formed substantially as a C-shape and is resiliently biased into a nominally closed O-shape position so as to encircle a generally cylindrical central region 103 extending along central axis A for closing open wounds in living tissue. End portion 106 extends circumferentially and overlaps end portion 108 at overlap area 110 to form a tubular structure. Preferably, the collar 100 has a rectangular cross-section wherein the width of the collar is greater than its height, to maximize the overlap area 110.

Central region 103 of the tubular structure should be large enough to permit the collar 100 to close a wound while its end portions 106, 108 overlap. An inner surface 104 of the collar 100 can be smooth, or it can be grooved, have protrusions, or be otherwise textured in some way, to create a roughened surface area to enhance contact between the collar and any tissue therein.

An outer surface 102 of the collar 100 is generally smooth, but may include energy directors 114 at the end portion 108. The energy directors 114 focus energy applied at the overlap area 110 of the collar 100 to insure that welds are formed preferentially at the overlap area.

Figure 10:
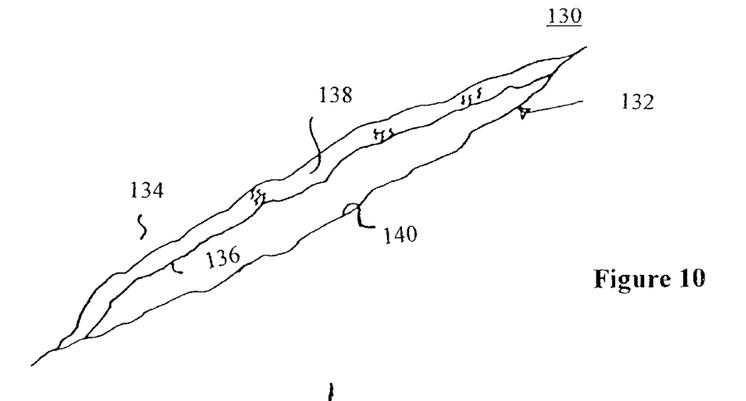
FIG. 10 is an oblique view of a wound or unwanted opening in a living tissue.
Figure 11:
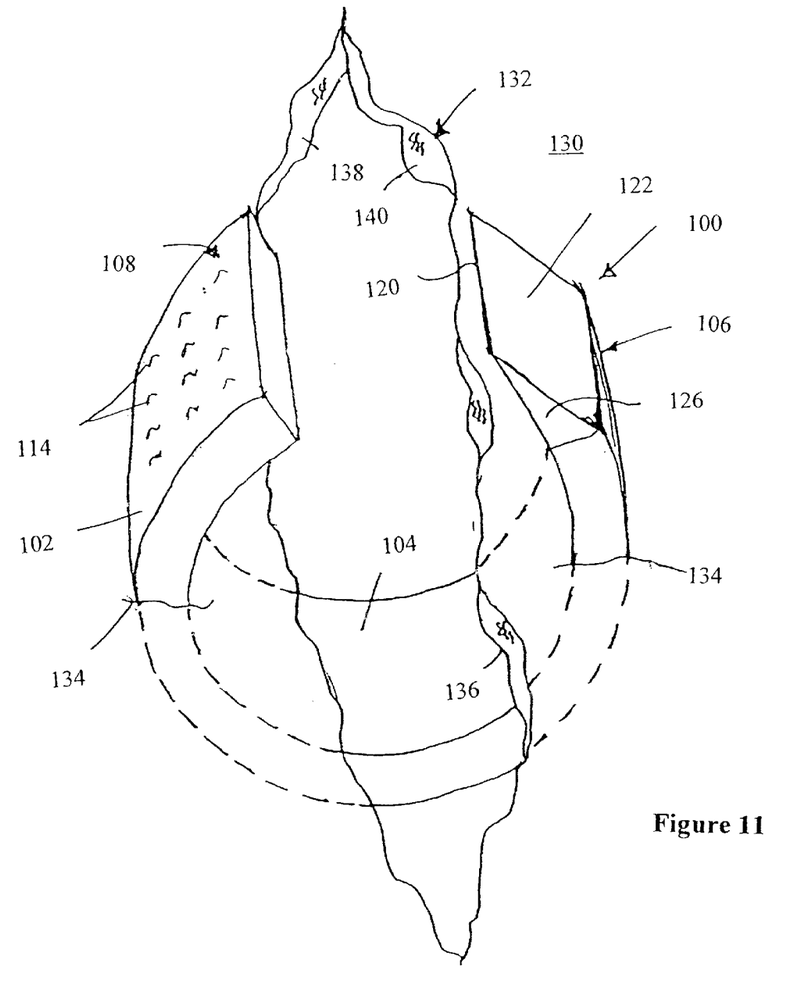
FIG. 11 is an oblique view of the end portion of the collar of FIG. 7 passing through the living tissue of FIG. 10 on either side of the wound.

An example of an open wound 132 in living tissue 130 is shown in FIG. 10. The wound 132 extends between opposite first and second surfaces 134, 136 of the tissue 130 and is defined by opposing first and second edges 138, 140 of the tissue. Referring also to FIG. 11, to close the wound 132 the collar 100 is first passed through the tissue 130 on opposite sides of the wound using the sharp edge 120 of the end portion 106 of the collar to penetrate the tissue. In particular, the sharp edge 120 is passed through the first surface 134 to the second surface 136 of the tissue 130, adjacent one of the edges 138, and then passed through the second surface 136 to the first surface 134 of the tissue, adjacent the other of the edges 140.

Figures 12, 13:
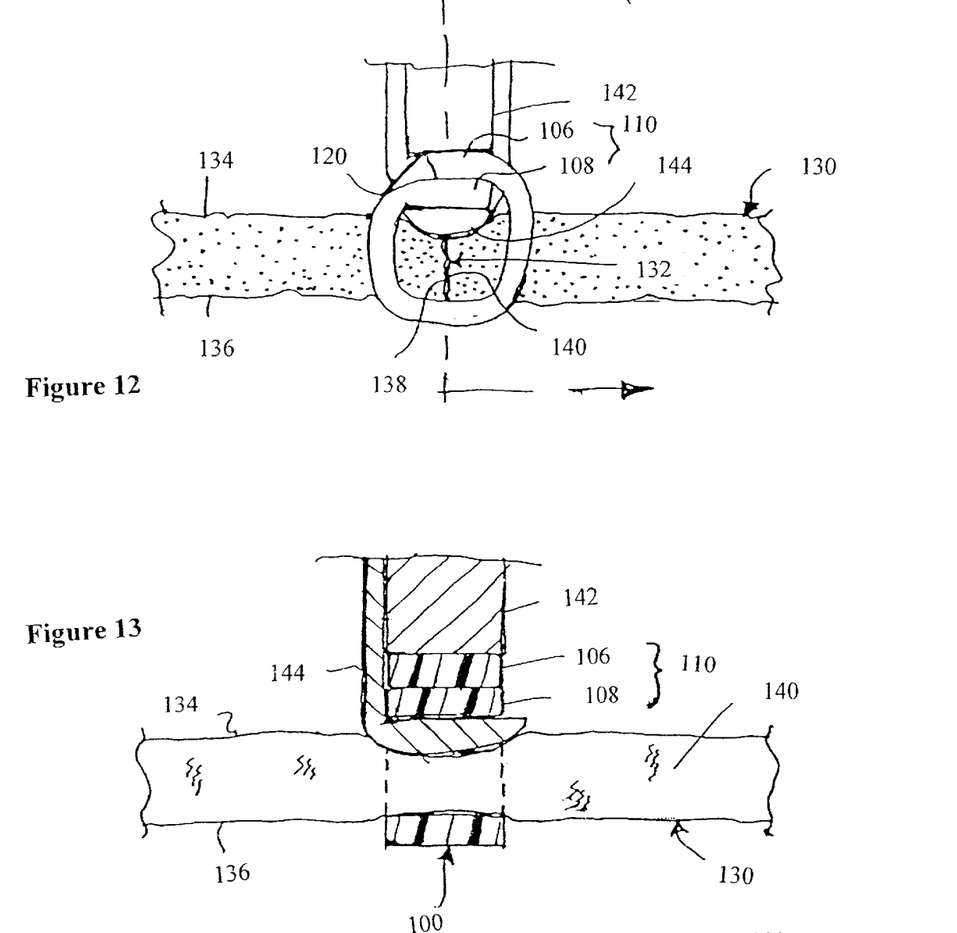
FIG. 12 is a side elevation view of an end effector of a fusing tool fusing overlapping end portions of the collar of FIG. 7 together to close the wound of the living tissue of FIG. 10.
FIG. 13 is a sectional view taken along line 13—13 of FIG. 12.

FIGS. 12 and 13 show the collar 100 after the end portions 106 and 108 of the collar have been overlapped to bring the edges 138, 140 of the wound 132 in the living tissue 130 together to close the wound. The overlap region 110 of the collar 100 is then compressed between a welding horn 142 and an anvil 144 of a fusing tool 220 similar to the fusing tool 20 of FIG. 3. As illustrated in FIGS. 12 and 13, the collar 100 and the fusing tool 220 comprise a kit 210, similar to the kit 200 in FIG. 4.

Figure 14:
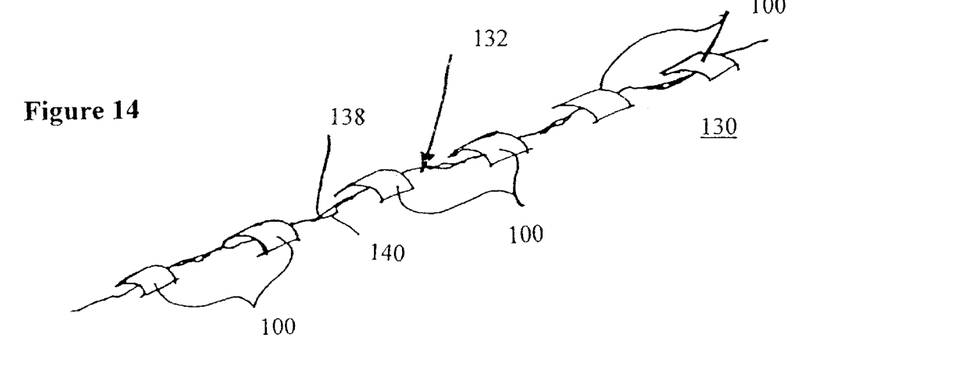
FIG. 14 is an oblique view of the wound of the living tissue of FIG. 10 closed with a plurality of fused collars similar to the collar of FIG. 7.

Ultrasonic or thermal energy is transferred from the welding horn 142 to the anvil 144 and the overlap area 110 of collar, creating localized heat, which melts the overlap area 110 of the collar 100 sufficiently to cause plastic flow and fusing of the end portions 106, 108. The fused overlap area 110 of the collar 100 remains compressed between the welding horn 142 and the anvil 144 for a short period to allow the fused end portions 106, 108 to re-solidify. FIG. 14 shows the edges 138, 140 of the wound 132 in the living tissue 130 secured together with a plurality of fused collars 100 to close and allow healing of the wound.

Referring back to FIGS. 7–9 and 11, at least one of the end portions 106 of the collar 100 includes the sharp edge 120 to allow penetration of the tissue 130 by the collar. Preferably, the sharp edge 120 is hardened in comparison to the remainder of the resiliently flexible collar 100. This hardening may be done, for example, by first compressing the end portion 106 in a die shaped to form the end portion into the sharp edge 120, and then by applying energy, e.g., ultrasonic welding, to the die and the end portion 106 to create localized heat. The heat melts the end portion 106 of the collar 100 into the specific shape of the die, i.e., the sharp edge 120, and the end portion is cooled quickly such that the end portion, and in particular the sharp edge, acquires a more rigid and inflexible constitution in comparison to the remainder of the collar 100.

As shown best in FIG. 8, the sharp edge 120 is formed by a localized top surface 122 of the end portion 106 converging, or tapering, towards, and joining a localized bottom surface 124 of the end portion 106. Preferably, the end portion 106 also includes localized side surfaces 126, 128 that are angled such that they become closer as they approach the sharp edge 120, as shown best in FIG. 9. The converging side surfaces 126, 128 assist the collar 100 in passing through tissue penetrated by the edge 120.

Figure 15:
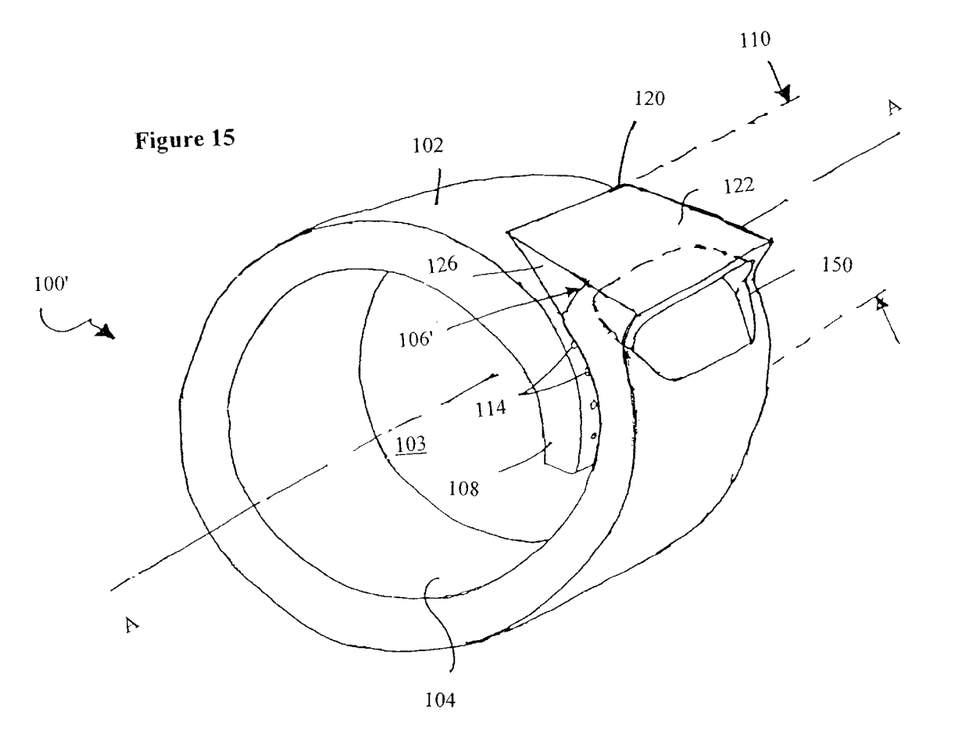
FIG. 15 is an oblique view of an alternative embodiment of the collar.

Referring to FIG. 15, another collar 100' according to the present disclosure is shown. The collar 100' of FIG. 15 is similar to the collar 100 of FIG. 7 and elements which are the same have the same reference numerals.

The collar 100' includes a pocket 150 for receiving a tip of a guide, such as a dull blade or dull needle for example, for forcing and guiding the collar 100' through living tissue. The guide could be straight and elongated, or curved and elongated, similar to needles for sutures. In particular, the pocket 150 is formed in an end portion 106' of the collar 100'. Alternatively, the collar 100' could be provided with an elongated pocket extending through the length of the collar from an open end at the end portion 108 to a closed end adjacent the sharp edge 120 in the end portion 106'. Many variants of the pocket 150 are possible.

Although preferred and other embodiments of the invention are described herein, further embodiments may be perceived by those skilled in the art without departing from the scope of the invention as defined by the following claims.

I claim:

1. A device for closure of a living tissue wound, comprising:
   a resiliently flexible and fusible collar having a C-shaped side profile disposed about a central region extending along a central axis, the C-shaped collar extending circumferentially between two end portions, the collar biasable into a nominally closed O-shape so that the end portions overlap, the overlapping end portions adapted to be fused together upon application of sufficient energy to at least one of the overlapping end portions, wherein at least one of the end portions of the collar has a sharp edge, wherein the sharp edge of the end portion is more rigid than the remaining portions of the collar prior to the end portions being fused.

2. A device according to claim 1 wherein the sharp edge of the end portion is made more rigid through heat treatment prior to use of the collar.

3. A device according to claim 1 wherein opposing side surfaces of the end portion with the sharp edge begin to converge towards the sharp edge.

4. A device according to claim 1 wherein opposing inner and outer circumferential surfaces of the end portion with the sharp edge converge at the sharp edge.

5. A device according to claim 1 wherein only one of the end portions has a sharp edge.

6. A device according to claim 1 wherein the energy applied to the collar is ultrasonic energy.

7. A device for closure of a living tissue wound, comprising:

a resiliently flexible and fusible collar having a C-shaped side profile disposed about a central region extending along a central axis, the C-shaped collar extending circumferentially between two end portions, the collar biasable into a nominally closed O-shape so that the end portions overlap, the overlapping end portions adapted to be fused together upon application of sufficient energy to at least one of the overlapping end portions, wherein at least one of the end portions of the collar has a sharp edge, and a pocket oriented towards the sharp edge for receiving a tip of a guide tool.

8. A device for closure of a living tissue wound, comprising:

a resiliently flexible and fusible collar having a C-shaped side profile disposed about a central region extending along a central axis, the C-shaped collar extending circumferentially between two end portions, the collar biasable into a nominally closed O-shape so that the end portions overlap, the overlapping end portions adapted to be fused together upon application of sufficient energy to at least one of the overlapping end portions, wherein at least one of the end portions of the collar has a sharp edge, wherein the collar further includes one or more protrusions located on one or more opposing circumferential surfaces of the end portions in the overlap area.

9. A device for closure of a living tissue wound, comprising:

a resiliently flexible and fusible collar having a C-shaped side profile disposed about a central region extending along a central axis, the C-shaped collar extending circumferentially between two end portions, the collar biasable into a nominally closed O-shape so that the end portions overlap, the overlapping end portions adapted to be fused together upon application of sufficient energy to at least one of the overlapping end portions, wherein at least one of the end portions of the collar has a sharp edge, wherein the collar is made of a thermoplastic polymeric material.

10. A device according to claim 9 wherein opposing side surfaces of the end portion with the sharp edge begin to converge towards the sharp edge.

11. A device according to claim 9, wherein opposing inner and outer circumferential surfaces of the end portion with the sharp edge converge at the sharp edge.

12. A device according to claim 9, wherein the collar further includes one or more protrusions located on one or more opposing circumferential surfaces of the end portions in the overlap area.

13. A device according to claim 9, the end portion with the sharp edge also includes a pocket oriented towards the sharp edge for receiving a tip of a guide tool.

14. A kit for closure of a tissue wound comprising:

a device for closure of a living tissue wound including a resiliently flexible and fusible collar having a C-shaped side profile disposed about a central region extending along a central axis, the C-shaped collar extending circumferentially between two end portions, the collar biasable into a nominally closed O-shape so that the end portions overlap, the overlapping end portions adapted to be fused together upon application of sufficient energy to at least one of the overlapping end portions, wherein at least one of the end portions of the collar has a sharp edge; and a fusing tool for compressing the collar and for applying energy to the collar to fuse the overlapped end portions together, wherein the fusing tool includes an energy source and a welding head for effecting the fusion.

15. A kit according to claim 14 wherein the energy source is an ultrasonic transducer, and the welding head includes a welding horn extending between the ultrasonic transducer and an anvil of the welding head for transmitting ultrasonic energy from the transducer to the anvil.

16. A method for closing a living tissue wound comprising providing a resiliently flexible and fusible collar having a C-shaped side profile disposed about a central region extending along a central axis, the C-shaped collar extending circumferentially between two end portions, wherein at least one of the end portions of the collar has a hardened sharp edge for tissue penetration;

forcing the sharp edge of the collar through the living tissue in a first direction adjacent one of edge of the wound;

forcing the sharp edge of the collar through the living tissue in a second direction, generally opposite the first direction, adjacent another edge of the wound, such that at least a portion of the two edges forming the tissue wound are positioned within the central region of the C-shaped collar;

biasing the collar into a nominally closed O-shape so that the end portions of the collar overlap and the tissue edges within the central region of the collar are substantially joined to close the tissue wound; and applying sufficient energy to the overlapped end portions of the collar so as to fuse the overlapped portions of the collar and maintain the closed wound.

17. A method according to claim 16, wherein the energy applied to the overlapping end portions of the collar is ultrasonic energy.

18. A method according to claim 16, wherein the collar is provided with a pocket oriented towards the sharp edge, and a tip of a guide tool is inserted into the pocket and the guide tool is used to force the sharp edge through the tissue.

19. A method according to claim 16 wherein the sharp edge of the end portion is made more rigid through heat treatment prior to use of the collar.

\* \* \* \* \*